Figure 1:
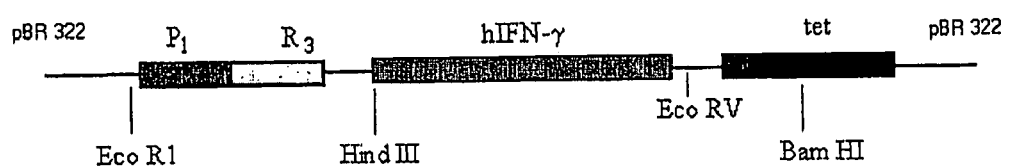

US007973133B2

(12) United States Patent
Ivanov et al.

(10) Patent No.: US 7,973,133 B2
(45) Date of Patent: Jul. 5, 2011

(54) INHIBITOR OF ENDOGENOUS HUMAN INTERFERON-GAMMA

(76) Inventors: Ivan Ivanov, Sofia (BG); Rumen Tsanev, Sofia (BG); Genoveva Nacheva, Sofia (BG); Hans-Guenther Grigoleit, Wiesbaden (DE); Rolf Gunther, Mainz (DE)

( * ) Notice: Subject to any disclaimer, the term of this patent is extended or adjusted under 35 U.S.C. 154(b) by 141 days.

(21) Appl. No.: 11/886,853

(22) PCT Filed: Oct. 5, 2005

(86) PCT No.: PCT/BG2005/000013
§ 371 (c)(1),
(2), (4) Date: Sep. 21, 2007

(87) PCT Pub. No.: WO2006/099701
PCT Pub. Date: Sep. 28, 2006

(65) Prior Publication Data

US 2009/0208452 A1 Aug. 20, 2009

(30) Foreign Application Priority Data

Mar. 21, 2005 (BG) ........................................ 109087

(51) Int. Cl.
*C07K 1/00* (2006.01)
*C07K 14/00* (2006.01)

(52) U.S. Cl. ........................................ 530/351; 530/350

(58) Field of Classification Search ........................ None
See application file for complete search history.

(56) References Cited

U.S. PATENT DOCUMENTS 5,451,658 A * 9/1995 Seelig ........................... 530/300
6,548,056 B2 * 4/2003 Presnell et al. .............. 424/85.7

FOREIGN PATENT DOCUMENTS

WO WO 94/12531 6/1994
WO WO 00/43033 7/2000

OTHER PUBLICATIONS

Luk et al. 1990. J. Biol. Chem. 265:13314-13319.*
Human interferon alpha in UniProtKB, http://www.uniprot.org/uniprot/?query=human+interferon+alpha&sort=score, downloaded Sep. 15, 2010.*
Nacheva Genoveva et al. "Human Interferon Gamma: Significance of the C-Terminal Flexible domain for its biological activity." Archives of Biochemistry and Biophysics, vol. 413, No. 1, May 1, 2003, pp. 91-98.

* cited by examiner

*Primary Examiner* — Shulamith H Shafer
(74) *Attorney, Agent, or Firm* — Jacobson Holman PLLC

(57) ABSTRACT

The invention relates to an inhibitor of endogenous human interferon-gamma (hIFN-ϝ) in autoimmune diseases, especially in multiple sclerosis. More precisely, the invention relates to inactivated protein derivatives of the hIFN-ϝ with preserved affinity to the hIFN-ϝ receptor. The derivatives represent genetically modified variants of hIFN-ϝ where the C-terminal part of the molecule is either deleted or replaced with a polypeptide sequence of another human protein and a recombinant hIFN-ϝ inactivated by physical or chemical methods.

1 Claim, 1 Drawing Sheet

though the exact etiology and pathogenesis of MS is still
INHIBITOR OF ENDOGENOUS HUMAN INTERFERON-GAMMA This is a 371 of PCT/BG2005/000013 filed Oct. 5, 2005.

FIELD OF INVENTION

The invention relates to an inhibitor of endogenous human interferon-gamma (hIFN-γ), applicable for treatment autoimmune diseases, especially for multiple sclerosis.

BACKGROUND OF INVENTION

About 2% of the human population is affected by various autoimmune diseases, including multiple sclerosis (MS). MS is neurodegenerative disease affecting the central nervous system (CNS) and leading to a progressive physical disability. Although the exact etiology and pathogenesis of MS is still obscure, it is believed that it might be autoimmune disease [1]. Histopathology of MS is characterized with demyelination of motor neurons in CNS, loss of oligodendrocytes and moderate inflammatory reaction. Affected areas in the brain are usually infiltrated with T-lymphocytes and macrophages. T-lymphocytes belong to the CD+ subtype and are characterized with increased production of Th1 cytokines (IL-2 and IFN-γ) [2]. As a result, the mononuclear cells are induced to produce increased amounts of some destructive substances such as lymphotoxines (LT) and tumor necrosis factor alpha (TNF-α). Many studies show that the abnormal production of IFN-γ plays a key role in the pathogenesis of MS [3-6].

Recombinant DNA technology reveals new approaches for neutralizing the activity of endogenous hIFN-γ to find application for treatment of autoimmune diseases including MS. An inhibitor of the hIFN-γ secretion is hIFN-β, which has already been applied for treatment of MS patients [U.S. Pat. No. 4,695,623, U.S. Pat. No. 4,897,471, WO9530435, CA2361081]. Patents RU2073522, RU2187332, RU02166959 recommend treatment with a mixture of hIFN-α, hIFN-β and hIFN-γ. It is reported, however, that the high daily doses of hIFN-β (8×106 IU) results in unfavorable consequences related with the following effects of hIFN-β: a) hIFN-β blocks the T-cells proliferation [7]; b) hIFN-β neutralizes IL-12 thus enhancing the effect of hIFN-γ on dendrite cells [8]; hIFN-β suppresses the activity of T cells, producing hIFN-γ and IL-4, thus lowering the level of CD4+ cells (Th1, Th2) and CD8+ (Tcl) cells without changing the ratio Th1/Th2 [9, 10]; d) after a short-term treatment of MS patients during the acute phase hIFN-β decreases the expression of pro-inflammatory cytokines (such as hIFN-γ and hIFN-α) and increases the expression of anti-inflammatory cytokines (IL-4 and IL-10) [11].

Another approach for healing MS patients consists in neutralizing the endogenous hIFN-γ by specific monoclonal antibodies [12, 13, W00145747]. The long-term treatment with anti-hIFN-γ antibodies, however, results in deterioration of the health conditions, probably because of weakening of the natural defense system.

U.S. Pat. No. 0,086,534 and CA2299361 offer a different approach for suppressing the abnormal production of IFN-γ based on the so called consensus interferons (IFN-con$_1$, IFN-con$_2$ and IFN-con$_3$) belonging to the groups of hIFN-α, hIFN-β and hIFN-τ. These recombinant preparations, however, show side effects, including toxicity.

Proteins with amino acid sequence partly coinciding with that of the hIFN-γ have been applied as antiviral, antitumor and immunomodulating agents [U.S. Pat. No. 4,832,959, WO0208107, AT393,690]. Their effects, however, is hard to be assessed since the descriptions are not supported with experimental data.

DESCRIPTION

The invention relates to an inhibitor of endogenous human interferon-gamma (hIFN-γ) in autoimmune diseases, especially in multiple sclerosis. More precisely, the invention relates to inactivated protein derivatives of the hIFN-γ with preserved affinity to the hIFN-γ receptor. These inactivated protein derivatives of the hIFN-γ represent genetically modified variants of hIFN-γ, where the C-terminal part of the molecule is either deleted or replaced with a polypeptide sequence of another human protein (e.g. hIFN-α) and a recombinant hIFN-γ, inactivated by physical or chemical methods.

The inactivated protein derivatives of the hIFN-γ according to the invention are constructed on the basis of both the spatial structure and functional map of hIFN-γ. Since the receptor binding sites are located in the N-terminal region, the primary structures of the inactivated protein derivatives according to the invention coincides with that part of the hIFN-γ molecule.

1. Genetically Modified Variants of hIFN-γ where the C-terminal Part of the Molecule is Deleted (Truncated hIFN-γ)

To construct a genetically modified variant where the C-terminal part of hIFN-γ is deleted, two oligonucleotides are synthesized and used as a primers for polymerase chain reaction (PCR). Nucleotide sequence of the forward primer (SEQ ID No:1) coincides with that of the 5' coding sequence of the hIFN-γ gene and is designed to introduce a HindIII cloning site. The reverse primer (SEQ ID No: 2) covers the cutting site at the 3' terminus of hIFN-γ gene (27 codons upstream from the stop codon) and introduces a BamHI cloning site. The truncated hIFN-γ gene (coding for 116 aminoacid residues) is prepared by a two step PCR using a full size synthetic human hIFN-γ gene (BG75781) as a template and the two above mentioned synthetic primers and cloned in the expression vector $pJP_1R_3$ (FIG. 1). *E. coli* LE392 are transformed and the yield of recombinant product is determined by ELISA. The truncated hIFN-γ is purified by two step (hydrophobic/cationic) chromatography as it is already described [EP0446582]. The activity of the truncated IFN-γ is determined by its antiviral activity (protecting effect of hIFN-γ on WISH cells against the cytopatic action of the vesicular stomatitis virus (VSV) [14]. The obtained results show that the truncated hIFN-γ is deprived of antiviral activity and is capable of competing with the full size protein for the hIFN-γ receptor.

2. Genetically Modified Variants of hIFN-γ where the C-terminal Part of the Molecule is Replaced with a Polypeptide Sequence of Another Human Protein (Hybrid hIFN-γ/hIFN-α protein)

The genetically modified variants of hIFN-γ where the C-terminal part of the molecule is substituted, represent a hybrid molecule where 27 aminoacids originating from a human proteins such as IFN-α, IFN-β, IL-2, etc. are substituted at the C-terminal part of the human IFN-γ. The size of the hybrid protein is 143 aminoacid residues (equal to that of the human IFN-γ). The hybrid IFN-γ/IFN-α gene is constructed by ligation of two DNA molecules one of which (containing 116 codons) originates from the 5'-terminal part of the hIFN-γ gene and the other (containing 27 in frame codons) comes from the 3'-terminal part of the IFN-α gene. The two gene fragments are prepared by PCR using full size hIFN-γ and hIFN-α genes as templates and a set of four synthetic primers. The forward primer for the hIFN-γ gene (SEQ ID No: 3) is designed to introduce a HindIII site at the 5'-terminus and the reverse primer (SEQ ID No:) to introduce a EcoRI site and also to eliminate the last 27 codons from the 3'-terminus of the hIFN-γ gene. The forward primer designed for modification of the IFN-α gene (SEQ ID No: 5) introduces an EcoRI site at the 5'-terminus of the IFN-α gene fragment and also to remove all but the last 27 codons from the IFN-α gene. The reverse primer (SEQ ID No: 6) introduces a stop-codon (TAA) and a BamH1 cloning site at the 3'-end of the IFN-α gene fragment. The two gene fragments are amplified by PCR, purified by agarose gel electrophoresis and ligated to each other and then to the expression vector $pJP_1R_3$. The expression plasmid thus obtained (containing the hybrid hIFN-γ/hIFN-α gene) is transformed into *E. coli* LE392 cells. Bacteria are cultivated and the hybrid protein is purified as described above. The antiviral test shows that the hybrid hIFN-γ/hIFN-α protein is devoid of antiviral activity on WISH cells and competes successfully with the intact hIFN-γ for the hIFN-γ receptor.

3. hIFN-γ Inactivated by Irradiation with UV Light (Photoinactivated hIFN-γ)

hIFN-γ contains single tryptophan (Trp) residue, which is indispensable for its biological activity. This residue is destroyed as follows: Recombinant IFN-γ is irradiated with UV light at 290 nm for 15 min. The results show that the biological activity of the photoinactivated hIFN-γ decreases drastically and the inactivated protein competes successfully with the intact hIFN-γ for its receptor.

Biological tests with the three derivative compounds of the hIFN-γ according to the invention show undoubtedly that they all have their basic biological activities (antiviral and antiproliferative) lost or drastically decreased and also that they all compete with hIFN-γ for the hIFN-γ receptor. Due to these properties, the inactive hIFN-γ derivative compounds can be used for suppression of the endogenous hIFN-γ activity. Since this effect is dose dependent, the activity of the endogenous hIFN-γ can be modulated by varying blood concentration of the hIFN-γ derivative proteins. This approach is applicable in the cases when the overproduction of endogenous hIFN-γ causes health problems as in the case of autoimmune diseases, including MS.

BRIEF DESCRIPTION OF THE FIGURES

FIG. 1 represents vector for expression of the hIFN-γ derivative, where:

$P_1$ is a synthetic phage promoter $R_3$ is a synthetic ribosome binding site.

The following examples illustrate the present invention without limiting its scope and spirit:

EXAMPLE 1

Truncated Human hIFN-γ

Truncated human hIFN-γ protein composed of 116 aminoacid residues is obtained by expressing of a truncated hIFN-γ gene in *E. coli* LE392 cells. The latter is prepared by PCR using a synthetic full size hIFN-γ gene as a template and two synthetic forward and reverse primers (SEQ ID No: 1 and SEQ ID No: 2). The two primers are synthesized on a Cyclon Plus (MilliGene) gene synthesizer by the phosphoramidite method (0.2 μmole scale) and purified by electrophoresis in 15% urea-polyacrylamide gel.

The truncated IFN-γ gene is prepared by two-step PCR amplification under the following conditions:

TABLE 1

Conditions for PCR

| Programme | Number of cycles | Time | Temperature |
|---|---|---|---|
| I | 1 | 5 min | 92° C. |
| II | 5 | 1 min | 92° C. |
| | | 1 min | 60° C. |
| | | 1 min | 72° C. |
| III | 35 | 1 min | 92° C. |
| | | 1 min | 65° C. |
| | | 1 min | 72° C. |
| IV | 1 | 10 min | 72° C. |

TABLE 2

Composition of the reaction mixture

| Substances | Quantity |
|---|---|
| Tamplate DNA (50 pg/μl) | 1 μl |
| Reverse primer (20 pmol/μl) | 1 μl |
| Forward primer (20 pmol/μl) | 1 μl |
| Taq-polymeraze (3 U/μl) | 1 μl |
| 10 x PCR buffer | 2 μl |
| 2 mM dNTP's | 2 μl |
| $dH_2O$ | 12 μl |
| Total | 20 μl |

The amplified DNA is digested with HindIII and BamHI, purified by agarose gel electrophoresis and cloned in the expression vector $pJP_1R_3$ (FIG. 1). To this end 20 μg plasmid DNA is dissolved in 150 μl HindIII buffer and digested with 20 U HindIII for 3 h at 37° C. Reaction mixture is extracted consecutively with phenol and chloroform and the DNA is precipitated with ethanol. DNA is dissolved in 150 μl BamHI buffer containing 20 U BamHI for 3 h at 37° C. The latter enzyme is inactivated by heating at 65° C. for 10 min and the vector DNA is dephosphorylated with 1 μl (1 U/μl) calf intestinal alkaline phosphatase (Boehringer Mannhein) for 30 min at 37° C. Reaction is stopped by adding 1/10 v/v 10×STE buffer (100 mM Tris, 1 M NaCl, 10 mM EDTA, 10% SDS) followed by deproteinization with phenol and chloroform. DNA is then precipitated with ethanol and purified by agarose gel electrophoresis.

Ligation reaction is carried out overnight at 4° C. at a molar ratio of vector to fragment DNA 3:1 and the ligation mixture is used for transformation of *E. coli* LE392 cells. The recombinant bacteria thus obtained are cultivated in LB medium (1% bacto-trypton, 0.5% yeast extract and 1% NaCl). LB agar is prepared by dissolving 1.5% bacto-agar in LB.

Primary transformants are selected in LB containing 50 μg/ml ampicillin following by cultivation on LB agar supplemented with 10 μg/ml tetracycline. The level of expression of the truncated IFN-γ gene is evaluated by ELISA using IFN-γ specific monoclonal antibodies. The truncated IFN-γ is purified by two step chromatography on C8-Sepharose and CM-Sepharose as described in EP0446582 B1. Antiviral activity (in international units) is determined by the protective effect of IFN-γ on WISH cells against the cytopatic action of stomatitis vesicular virus (VSV) as recommended by Forti et al. [14]. Analyses show that the truncated IFN-γ is devoid of any antiviral activity.

EXAMPLE 2

Construction of a Hybrid IFN-γ/IFN-α Protein

The hybrid protein hIFN-γ/hIFN-α comprising 143 aminoacid residues consists of two N- and C-terminal parts: hIFN-γ (composed of 116 aminoacids) and hIFN-α (composed of 27 aminoacids). This protein is product of a hybrid hIFN-γ/hIFN-α gene prepared by ligation of two DNA fragments containing 116 (5' terminal) hIFN-γ and 27 (3' terminal) hIFN-α codons respectively. The two DNA molecules are obtained by PCR using full size hIFN-γ and hIFN-α genes as templates and two sets of primers (SEQ ID No 3-6). The forward primer for modification of the hIFN-γ gene (SEQ ID No: 3) is designed to introduce a HindIII site at the 5' terminus (for ligation to the expression vector) and the reverse primer (SEQ ID No: 4) introduces EcoRI site at the 3' terminus (for ligation to the hIFN-α gene). The latter is designed also to eliminate the last 27 codons from the hIFN-γ gene. The forward primer for the hIFN-α gene (SEQ ID No: 5) carries a EcoRI site at the 5' terminus (for ligation to the hIFN-γ gene) and also to removes all but the last 27 codons from the hIFN-α gene. The reverse primer (SEQ ID No: 6) is designed to introduce a stop-codon (TAA) and a BamH1 site (for ligation to the expression vector) at the 3' end of the hIFN-α gene fragment.

PCR is carried out under conditions described in Tables 1 and 2 and the amplified DNA fragments are digested with HindIII and EcoRI for hIFN-γ and EcoRI and BamHI for hIFN-α respectively. The DNA fragments are further purified by agarose gel electrophoresis and ligated first to each other and then to the expression vector. The expression plasmid carrying the hybrid hIFN-γ/hIFN-α gene is transformed into *E. coli* LE392 cells. Bacteria are cultivated and the hybrid protein is purified as described in Example 1. The antiviral test shows that the hybrid protein is devoid of any antiviral activity.

EXAMPLE 3

Inactivation of hIFN-γ by UV Irradiation

Recombinant human hIFN-γ (purity higher than 99%) is dissolved in 0.14 M NaCl, 10 mM Tris, pH 7.4 and exposed in a quartz cuvette to UV light at 290 nm for 15 min. This treatment leads to photolysis of the unique tryptophan residue and to 100 fold decrease in the hIFN-γ antiviral activity.

EXAMPLE 4

Inhibitory Effect of Inactive hIFN-γ Derivative Proteins on the Biological Activity of Intact hIFN-γ

Inhibitory effect of inactive hIFN-γ derivative proteins on the biological activity of intact hIFN-γ is investigated using an amniotic cell line WISH (known to be rich of hIFN-γ receptors). To saturate the hIFN-γ receptors, WISH cells are pre-incubated with inactive hIFN-γ derivative proteins for 1 h. The proteins are washed out, the cells are treated with different concentrations of intact hIFN-γ and infected with VSV according to [14]. The obtained results show a strongest inhibitory effect for the truncated (116 aminoacids) hIFN-γ, followed by the hybrid hIFN-γ/hIFN-α protein and the UV-inactivated hIFN-γ. Since all hIFN-γ inactive derivative proteins preserve their affinity to the hIFN-γ receptor, they a capable of suppressing biological activity of endogenous (native) hIFN-γ.

REFERENCES

1. Waksman, B. H. and Reynolds W. E. (1984) Multiple sclerosis as a disease of immune regulation. Proc. Soc. Exp. Biol. Med., 175, 282-294.
2. Oto, A. S., Guarion, T. J., Driver, R., Steinman, L., Umetsu, D. T. (1996) Regulation of disease susceptibility: decreased prevalence of IgE-mediated allergic disease in patients with multiple sclerosis. J. Allergy Clin. Immunol. 97, 1402-8.
3. Johnson, K. P. (1988) Treatment of multiple sclerosis with various interferons: The cons. Neurology, 38 (suppl. 2) 52-64.
4. Martino, G., Moiola, L., Brambilla, E., Clementi, E., Comi, G., Grimaldi, L. M. (1995). Interferon gamma induces T lymphocyte proliferation in multiple sclerosis via a $Ca^{2+}$-dependent mechanism. J. Neuroimmunol. 62, 169-76.
5. Vartanian, V., Li, Y., Zhao, M., Stefansson, K. (1995) Interferon-gamma-induced oligodendrocyte cell death: implications for the pathogenesis of multiple sclerosis. Mol. Med. 1, 732-43.
6. Beck, J., Rondot, P., Catinot, L., Falcoff, E., Kirchner, H., Wietzerbin, J. (1988) Increased production of interferon gamma and tumor necrosis factor precedes clinical manifestation in multiple sclerosis: do cytokines trigger off exacerbations? Acta Neurol. Scand. 78, 318-323.
7. Rep, M. H., Hintzen, R. Q., Polman, C. H., van-Lier, R. A. (1996) Recombinant interferon-beta blocks proliferation but enhances interleukin-10 secretion by activated human T-cells. J. Neuroimmunol. 67, 111-8.
8. Heystek, H. C., den Drijver, B., Kapsenberg, M. L., van Lier, R. A., de Jong, E. C. (2003) Type I IFNs differentially modulate IL-12p70 production by human dendritic cells depending on the maturation status of the cells and counteract IFN-gamma-mediated signaling. Clin. Immunol. 107, 170-177.
9. Franciotta, D., Zardini, E., Bergamaschi, R., Andreoni, L., Cosi, V. (2003) Interferon gamma and interleukin 4 producing T cells in peripheral blood of multiple sclerosis patients undergoing immunomodulatory treatment. J. Neurol. Neurosurg. Psychiatry. 74, 123-126.
10. Furlan, R., Bergamim A., Lang, R., Brambilla, E., Franciotta, D., Martinelli, V., Comi, G., Paninam P., Martino. G. (2000) Interferon-beta treatment in multiple sclerosis patients decreases the number of circulating T cells producing interferon-gamma and interleukin-4. J. Neuroimmunol. 111, 86-92.
11. Khademi, M., Wallstrom, E., Andersson, M., Piehl, F., Di Marco, R., Olsson, T. (2000) Reduction of both pro- and anti-inflammatory cytokines after 6 months of interferon beta-la treatment of multiple sclerosis. J. Neuroimmunol. 103, 202-210.
12. Skurkovich, S., Boiko, A., Beliaeva, I., Buglak, A., Alekseeva, T., Smirnova, N., Kulakova, O., Tchechonin, V., Gurova, O., Deomina, T., Favorova, O. O., Skurkovic, B., Gusev, E. (2001) Randomized study of antibodies to IFN-gamma and TNF-alpha in secondary progressive multiple sclerosis. Mult. Scler. 7, 277-284.
13. Skurkovich, B., Skurkovich, S. (2003) Anti-interferon-gamma antibodies in the treatment of autoimmune diseases. Curr. Opin. Mol. Ther. 5, 52-57.
14. Forti, R. L., Schuffman, S. S., Davies, H. A. and Mitchell, W. M. (1986) Objective antiviral assay of the interferons by computer assisted data collection and analysis. Methods in Enzymol. 119, 533-540.

The invention claimed is:

1. An inhibitor of endogenous human interferon-γ (hIFN-γ) comprising an inactivated recombinant hIFN-γ protein having binding affinity for the hIFN-γ receptor and consisting of recombinant hybrid protein hIFN-γ/hIFN-α (human interferon-α), wherein the 27 amino acids at the C-terminal end of hIFN-α replaces the 27 amino acids at the C-terminal end of hIFN-γ.

* * * * *

UNITED STATES PATENT AND TRADEMARK OFFICE
CERTIFICATE OF CORRECTION

PATENT NO. : 7,973,133 B2  
APPLICATION NO. : 11/886853  
DATED : July 5, 2011  
INVENTOR(S) : Ivanov et al.

Page 1 of 1

It is certified that error appears in the above-identified patent and that said Letters Patent is hereby corrected as shown below:

ON THE TITLE PAGE:

Item (57) Abstract

Line 2 should be corrected from "hIFN-&gammad" to --hIFN-gamma--

Line 5 should be corrected, both occurrences, from "hIFN-&gammad" to --hIFN-gamma--

Line 7 should be corrected from "hIFN-&gammad" to --hIFN-gamma--

Line 9-10 should be corrected from "hIFN-&gammad" to --hIFN-gamma--

IN THE SPECIFICATIONS:

Page 1, line 40-41, left hand column, under Background of Invention:

Should be corrected from "It is reported, however, that the high daily doses of hIFN-β (8×106 IU) results..." to --It is reported, however, that the high daily doses of hIFN-β ($8 \times 10^6$ IU) results...--

Signed and Sealed this  
Thirtieth Day of August, 2011

David J. Kappos  
*Director of the United States Patent and Trademark Office*

SEQUENCE LISTING

<160> NUMBER OF SEQ ID NOS: 5

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
cccaagctta tgcaggacc                                                    19

<210> SEQ ID NO 2
<211> LENGTH: 29
<212> TYPE: DNA
<213> ORGANISM: Artificial
<220> FEATURE:
<223> OTHER INFORMATION: Primer

<400> SEQUENCE: 2
cgcggatcct tacacttgga tgagttcat                                         29

<210> SEQ ID NO 3
<211> LENGTH: 26
<212> TYPE: DNA
<213> ORGANISM: Artificial
<220> FEATURE:
<223> OTHER INFORMATION: Primer

<400> SEQUENCE: 3
ccggaattcc acttggatga gttcat                                            26

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ccggaattcg aggttgtcag a                                                 21

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
cgcggatcct tattccttcc tc                                                22